(12) United States Patent
Satake et al.

(10) Patent No.: US 10,139,369 B2
(45) Date of Patent: Nov. 27, 2018

(54) MASS SPECTROMETER

(71) Applicant: HITACHI HIGH-TECHNOLOGIES CORPORATION, Tokyo (JP)

(72) Inventors: Hiroyuki Satake, Tokyo (JP); Hideki Hasegawa, Tokyo (JP); Masao Suga, Tokyo (JP); Yuichiro Hashimoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 17 days.

(21) Appl. No.: 15/534,607

(22) PCT Filed: Dec. 24, 2014

(86) PCT No.: PCT/JP2014/084054
§ 371 (c)(1),
(2) Date: Jun. 9, 2017

(87) PCT Pub. No.: WO2016/103341
PCT Pub. Date: Jun. 30, 2016

(65) Prior Publication Data
US 2017/0336357 A1    Nov. 23, 2017

(51) Int. Cl.
*G01N 27/62* (2006.01)
*H01J 49/04* (2006.01)

(52) U.S. Cl.
CPC ............ *G01N 27/624* (2013.01); *H01J 49/04* (2013.01)

(58) Field of Classification Search
CPC .............................. G01N 27/624; H01J 49/04
USPC .......................... 250/281, 282, 283, 288, 290
See application file for complete search history.

(56) References Cited

U.S. PATENT DOCUMENTS

| | | | |
|---|---|---|---|
| 5,449,902 | A | 9/1995 | Onishi et al. |
| 2008/0087814 | A1 | 4/2008 | Loucks |
| 2008/0224033 | A1 | 9/2008 | Makarov |
| 2010/0230588 | A1* | 9/2010 | Atkinson ............ G01N 27/624 250/283 |
| 2010/0237233 | A1 | 9/2010 | Covey et al. |

(Continued)

FOREIGN PATENT DOCUMENTS

| | | |
|---|---|---|
| JP | 06-201650 A | 7/1994 |
| JP | 2012-521072 A | 9/2012 |
| WO | WO 2007/140400 | * 12/2007 .............. H01J 49/00 |

OTHER PUBLICATIONS

International Search Report of PCT/JP2014/084054 dated Jan. 27, 2015.

(Continued)

*Primary Examiner* — Nicole Ippolito
(74) *Attorney, Agent, or Firm* — Mattingly & Malur, PC

(57) ABSTRACT

A mass spectrometer device comprising an ion mobility separation device and a mass spectrometer that are coupled together. In order to achieve high efficiency, high throughput, and high sensitivity, the mass spectrometer is provided with: a first flow passageway 24 through which ions from an ion source 1 are introduced into the mass spectrometer 11 by passing through an ion mobility separation unit 2; a second flow passageway 21 through which the ions from the ion source are introduced into the mass spectrometer without passing through the ion mobility separation unit; and a switch means, such as shield units 4, 5, for switching between the first flow passageway 24 and the second flow passageway 21.

13 Claims, 13 Drawing Sheets

(56) References Cited

U.S. PATENT DOCUMENTS

2011/0253890 A1 10/2011 Belford et al.
2013/0187037 A1* 7/2013 Wu ..................... G01N 27/622
  250/282
2017/0307565 A1* 10/2017 Clemmer ............. G01N 27/622

OTHER PUBLICATIONS

German Office Action received in corresponding German Office Action received in corresponding Germany Application No. 11 2014 007 155.2 dated Jul. 21, 2018.

* cited by examiner

MASS SPECTROMETER

TECHNICAL FIELD

The present invention relates to a mass spectrometer device equipped with an ion mobility separation device.

BACKGROUND ART

A mass spectrometer device can be used to separate ions in vacuum depending on the mass to charge ratio (m/z) of molecular ions, whereby ions can be separated and detected with high sensitivity and high accuracy. During mass spectrometry, ions are separated according to the mass to charge ratio (m/z). The mass spectrometry technology is commonly employed in liquid chromatograph (LC) or gas chromatograph (GC) detectors, in which analysis techniques referred to as liquid chromatography mass spectrometry (LC/MS) or gas chromatography mass spectrometry (GC/MS) are often used. In recent years, developments have been made tandem mass spectrometry which resolves ions to be measured and measures the resolved ions to enable separation from other contaminating ions; high-resolution mass spectrometer devices, such as a time-of-flight mass spectrometer device and a Fourier transform mass spectrometer device; and high-sensitivity mass spectrometer devices, such as a triple-quadrupole mass spectrometer device and a quadrupole mass spectrometer device. Accordingly, the use of mass spectrometers is becoming increasingly more widespread, particularly in the fields of biotechnology and medicine.

Meanwhile, an ion mobility separation device (or an ion mobility device) separates ions by utilizing the difference in ion transfer velocity in gaseous phase depending on the three-dimensional structure of molecular ions, in gaseous phase under atmospheric pressure. Accordingly, in principle, ions of structure isomers having the same mass to charge ratios (m/z), which are difficult to separate by mass spectrometry, can be separated. Because the ion mobility separation device thus provides a different separating performance from mass spectrometry, measurement methods have been reported that combine a mass spectrometer device and an ion mobility separation device. An ion mobility method is implemented in an asymmetric field-applying ion mobility separation device (FAIMS or DMS (Differential mobility spectrometry)).

Patent Literature 1 discloses an example of the device combining a FAIMS and a mass spectrometer device. The FAIMS is attached in a stage preceding the mass spectrometer device, and configured such that the user can attach or detach the FAIMS. Patent Literature 2 discloses other examples of a FAIMS and a mass spectrometer device. An internal electrode of the FAIMS has a cylindrical shape and can be rotated. It is indicated that in this configuration, a mode in which mass spectrometry is performed after ion separation (hereafter referred to as "ion separation mode") and an MS mode in which ion separation is not performed in the FAIMS can be switched by rotating the internal electrode of the FAIMS. In the MS mode, a cylindrical flow passageway bored in the internal electrode also becomes passable.

CITATION LIST

Patent Literature

Patent Literature 1: JP 2012-521072 A
Patent Literature 2: US 2011/0253890 A1

SUMMARY OF INVENTION

Technical Problem

In a device combining the ion mobility separation device that performs separation and detection by ion mobility and the mass spectrometer device that separates ions by mass (m/z), a technique for detecting, with high separation performance and high throughput, ions generated by an ion source is important. However, there are currently the following problems. In the following description, the ion mobility separation device will be described as being a FAIMS by way of example.

By the method according to Patent Literature 1, in the configuration in which the FAIMS is mounted, ion separation by the FAIMS is possible, so that the separating performance of the system as a whole can be increased by, e.g., noise removal. On the other hand, ions will pass through the FAIMS having narrow plate electrodes, resulting in ion loss and a decrease in the amount of ions that reach the detector. The ion loss is caused simply by the mounting of the FAIMS, regardless of whether the ion separation function of the FAIMS is turned ON or OFF. Accordingly, there is the significant problem of a decrease in sensitivity in the mass spectrometry mode in which the separation function of the FAIMS is turned OFF (hereafter "MS mode").

If the sample to be measured does not require the ion separation function of the FAIMS, it is effective to detach the FAIMS. This is because, as mentioned above, ion loss is caused simply by the mounting of the FAIMS. However, removing the FAIMS manually by the user, as in Patent Literature 1, will normally take several minutes to several tens of minutes. Accordingly, performing the attaching and detaching operations for each sample to be measured is cumbersome, and the throughput of measurement may even be decreased.

By the method according to Patent Literature 2, the electrode is rotated to switch the flow passageways, and the switching takes time. Even with an automatically controlled drive system, several seconds to several tens of seconds will be required. In the case of manual operation, several minutes would be required. A rotation drive system is also required.

In view of the above-described circumstances, the present invention provides a mass spectrometer device for performing an analysis using an ion mobility separation device efficiently.

Solution to Problem

A mass spectrometer device according to the present invention includes an ion source; an ion mobility separation unit; a mass spectrometer; a first flow passageway for causing ions from the ion source to be introduced into the mass spectrometer by passing through the ion mobility separation unit; a second flow passageway for causing the ions from the ion source to be introduced into the mass spectrometer without passing through the ion mobility separation unit; and a blocking mechanism for selectively blocking the passage of the ions from the ion source through the first flow passageway or the second flow passageway. An introduction opening of the first flow passageway and an introduction opening of the second flow passageway are disposed at equivalent distances from the ion source.

The blocking mechanism may be configured of a shield means using an electric field, gas, or an object, or combinations thereof.

According to an aspect of the present invention, during analysis in the mass spectrometer of the ions that have passed through the second flow passageway, upon detection of a peak of an ion having a mass to charge ratio that has been registered in advance, the blocking mechanism may block the second flow passageway and allow the ion to pass through the first flow passageway.

According to another aspect of the present invention, during analysis in the mass spectrometer of the ions that have passed through the second flow passageway, upon detection of a peak with a mass spectrum S/N smaller than or equal to a pre-set threshold value, the blocking mechanism may block the second flow passageway and allow the ions to pass through the first flow passageway.

Advantageous Effects of Invention

According to the present invention, a highly efficient, high-throughput, and highly sensitive analysis can be implemented in a device using an ion mobility separation device and a mass spectrometer device.

The additional features of the present invention will become apparent from the following description and the attached drawings. Objects, configurations, and effects other than those mentioned above will become apparent from the following description of examples.

DESCRIPTION OF EMBODIMENTS

In the following, examples of the present invention will be described with reference to the attached drawings. The attached drawings illustrate specific examples in accordance with the principles of the present invention. The examples, however, are described for the purpose of facilitating an understanding of the present invention, and are not to be used for interpreting the present invention in a limiting sense.

Figure 1A:
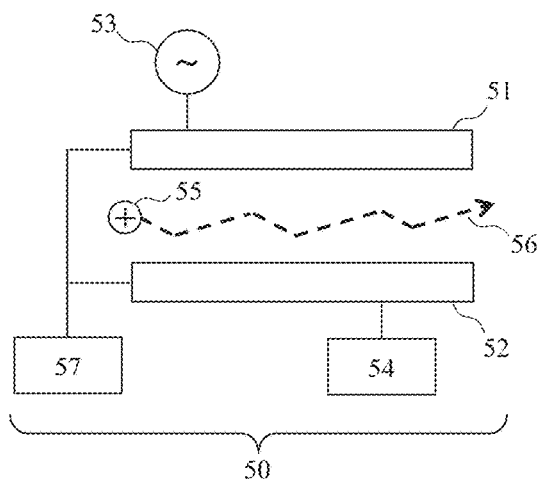
FIG. 1A is a schematic diagram illustrating a conventional configuration of a FAIMS.

FIG. 1A is a schematic diagram illustrating a conventional configuration of a FAIMS. The FAIMS 50 is provided with two metal plate electrodes, a first electrode 51 and a second electrode 52. The two electrodes are spaced apart by a distance of approximately 0.1 mm to several mm, and have an electrode length, which corresponds to the distance of travel of ions, of approximately several tens of mm. In recent years, there have also appeared FAIMSs having finer structures, some with a distance between electrodes on the order of several 10 μm.

Figure 1B:
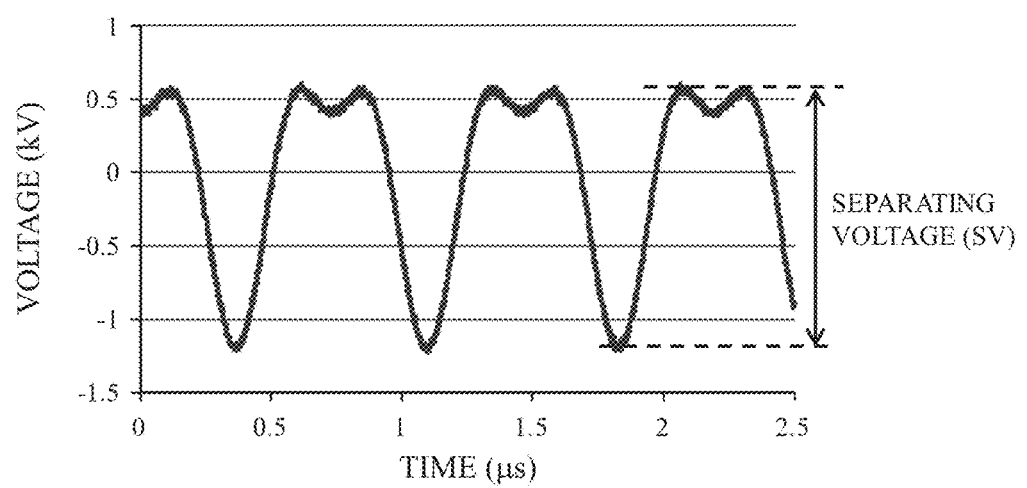
FIG. 1B illustrates the waveform of a separating voltage in the FAIMS.

The FAIMS is provided with an alternating-current voltage power supply 53, a direct-current voltage power supply 54, and a bias voltage power supply 57. In the FAIMS, using the alternating-current voltage power supply 53, a separating voltage (or a dispersing voltage, or a separation voltage: SV) superposed with a high frequency voltage is applied to the first electrode 51, thereby to apply a high frequency electric field between the first electrode 51 and the second electrode 52. FIG. 1B illustrates an example of the separating voltage, where the separating voltage (SV) consists of a high voltage (plus voltage) and a low voltage (minus voltage) which are applied repeatedly at certain periods so as to be zero when averaged over time. The separating voltage has a voltage amplitude of several 100 V to several kV. In addition, by applying a compensating voltage (or a correction voltage, or a compensation voltage: CV), which is a direct-current voltage generated by the direct-current voltage power supply 54, to the second electrode 52, an ion trajectory 56 of a certain specific ion 55 is corrected and a specific ion 55 alone is transmitted, and the other ions can be eliminated. The compensating voltage is on the order of −100 V to +100 V. The direct-current voltage by the direct-current voltage power supply 54 may also be applied to the first electrode 51. Similarly, the separating voltage may be applied to the second electrode 52. As a bias voltage is applied by the bias voltage power supply 57 to the first electrode 51 and the second electrode 52, ions are efficiently introduced from electrodes in a stage preceding the FAIMS 50, and ions are efficiently discharged to electrodes in the stage subsequent to the FAIMS 50. The present invention may be implemented in a similar manner not just in the FAIMS but also in other ion mobility separation devices, and the application of the present invention is not limited to the FAIMS.

In the examples of the present invention, an embodiment will be described in which, in a mass spectrometer provided with a first ion flow passageway (ion separation mode) that passes through a FAIMS and a second ion flow passageway (MS mode) that does not pass through the FAIMS, flow passageway switching to determine which of the flow passageways ions should pass through, i.e., analysis mode switching, is performed. The MS mode is the mode in which mass spectrometry alone is performed without passing through the FAIMS. The ion separation mode is the mode in which the FAIMS is used for ion separation, and further mass spectrometry is performed. The MS mode has the feature of being able to pass all ions through the mass spectrometer without selectivity, whereby a target molecule search can be conducted, and high sensitivity detection is possible. On the other hand, in the ion separation mode, only a certain target ion is passed through the FAIMS, so that the ion can be detected with high sensitivity and high S/N. Accordingly, by choosing the analysis mode as described in the examples, mass spectrometry can be performed with high efficiency.

First Example

A first example will be described. In the present example, as a blocking mechanism for switching the analysis modes by selectively blocking the passage of ions from an ion source through the first flow passageway or the second flow passageway, a physical means of a shield unit, such as a shutter, is used.

Figure 2:
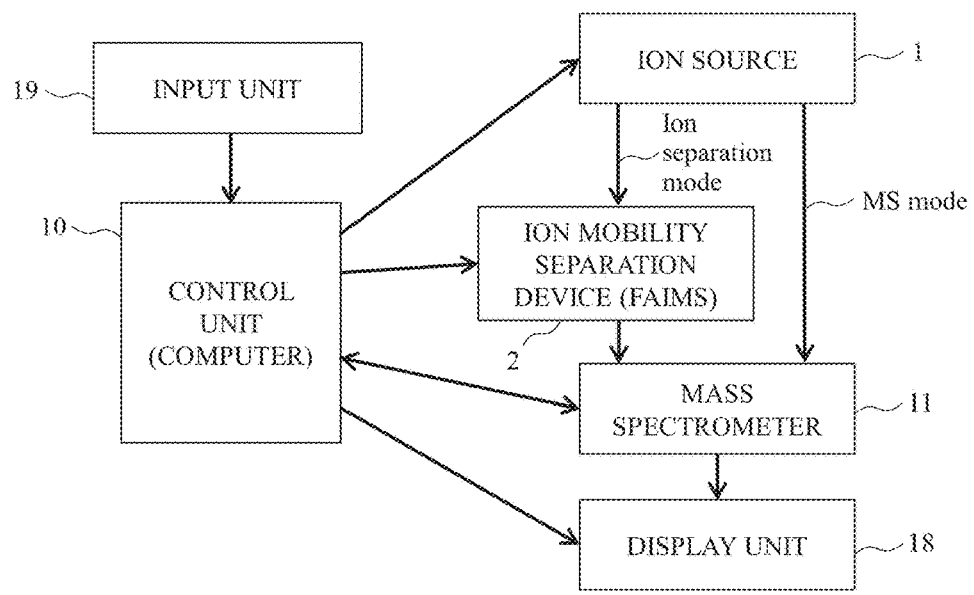
FIG. 2 illustrates a configuration of a mass spectrometer device.

FIG. 2 illustrates a configuration of a mass spectrometer device in which a FAIMS, which is an ion mobility separation device, and a mass spectrometer are used. Ions generated by an ion source 1 are subjected to analysis and detection in two analysis modes. One is the ion separation mode in which ion separation is performed in the FAIMS 2, which is an ion mobility separation device, and then mass spectrometry is performed in a mass spectrometer 11. The other is the MS mode in which mass spectrometry is performed in the mass spectrometer 11 without performing ion separation in the FAIMS 2.

A control unit 10 controls various constituent elements of the FAIMS and the mass spectrometer, and is configured from an information processing device, such as a personal computer. The control unit 10 is provided with a central processing device, an auxiliary storage device, a main storage device, a display unit 18, and an input unit 19. The central processing device is configured from a processor (which may be referred to as a computing unit), such as a CPU, for example. The auxiliary storage device may include a hard disk, and the main storage device may include a memory. The display unit 18 is a display or the like for displaying an analysis spectrum, results, analysis conditions and the like. The input unit 19 includes a keyboard, a pointing device (such as a mouse) and the like, for the input of analysis conditions and the like.

Figure 3A:
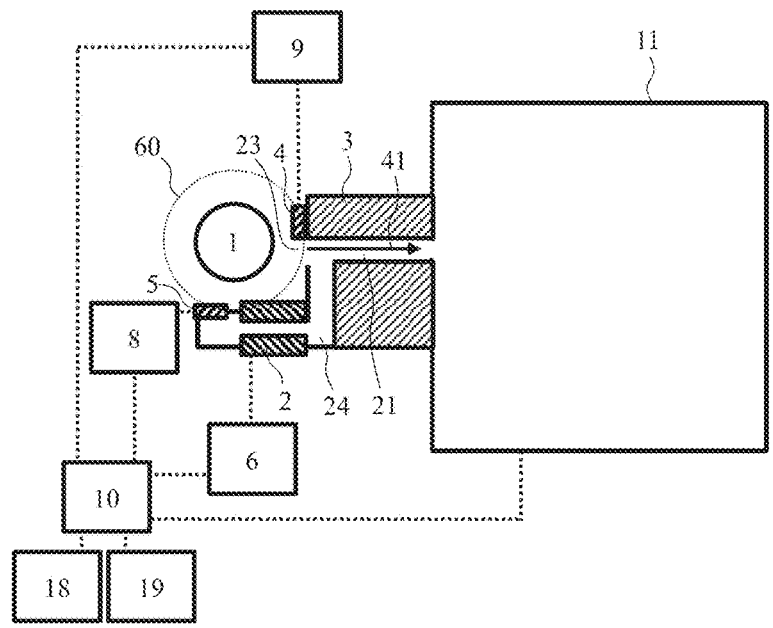
FIG. 3A is a schematic diagram illustrating a configuration example of the mass spectrometer device in MS mode.
Figure 3B:
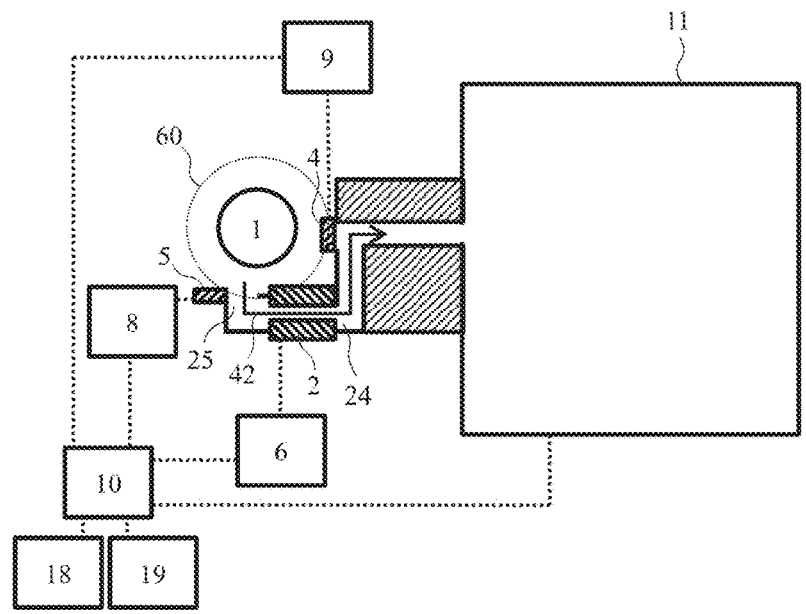
FIG. 3B is a schematic diagram illustrating a configuration example of the mass spectrometer device in ion separation mode.

FIG. 3A and FIG. 3B are partial cross sectional schematic diagrams illustrating the mass spectrometer device of the present example, as viewed from above. FIG. 3A illustrates the MS mode, and FIG. 3B illustrates the ion separation mode. The switching of the two analysis modes, i.e., the switching of the sample ion flow passageways, is performed by a blocking mechanism using a shield unit 4 and a shield unit 5. The sample ions produced by the ion source 1 enter either the ion introduction opening 23 or 25 in accordance with the analysis mode, and pass through the flow passageway 21 or the flow passageway 24. Then, the ions pass through a flow passageway 21 formed by an introduction opening electrode 3, enter the mass spectrometer 11, and analyzed therein. The flow passageway 21 formed by the introduction opening electrode 3 serves as a dividing wall between the atmospheric pressure and vacuum, and has a cylindrical shape with a diameter of approximately 0.1 mm to 1 mm. To the FAIMS 2, a separating voltage, a compensating voltage, and a bias voltage as described with reference to FIG. 1 are applied by a power supply 6 under the control of the control unit 10. For simplifying description, only one power supply 6 is illustrated. In the mass spectrometer 11, mass separation and detection is performed in accordance with the mass to charge ratio (m/z) of the ions.

In each of the two analysis modes, an ion flow passageway is present. In the MS mode, ions enter the introduction opening 23, pass through the flow passageway 21 without passing through the FAIMS 2, and enter the mass spectrometer 11, along an ion trajectory 41. On the other hand, in the ion separation mode, ions enter the introduction opening 25, pass through the flow passageway 24 passing through the FAIMS 2, and then enter the mass spectrometer 11 via the flow passageway 21, along an ion trajectory 42. In the present example, the flow passageway 24 is eventually integrated with the flow passageway 21, which is connected to the mass spectrometer.

The switching of the two analysis modes as to whether the ions are to enter the introduction opening 23 or the introduction opening 25 is performed by driving the shield unit 4 and the shield unit 5. In the MS mode, as illustrated in FIG. 3A, the shield unit 4 is opened, and the shield unit 5 is closed. As a result, the ions travel along the ion trajectory 41 via the introduction opening 23, and are introduced into the mass spectrometer 11. In the ion separation mode, as illustrated in FIG. 3B, the shield unit 4 is closed, and the shield unit 5 is opened. As a result, the ions travel along the ion trajectory 42 via the introduction opening 25, and are introduced into the mass spectrometer 11. The shield unit 4 is driven by a drive unit 9 under the control of the control unit 10. The shield unit 5 is driven by a drive unit 8 under the control of the control unit 10. Accordingly, by opening and closing the shield unit 4 and the shield unit 5, the flow passageway 21 or the flow passageway 24 can be selected to allow the ions to pass therethrough. For the shield units, a shutter, a shield plate, a lid, a plug and other equivalent existing technologies may be used, as long as the configuration is capable of blocking gases and ions. In particular, in order to completely block the passage of gases, hermetically sealable structures, such as rubber rings and other existing sealing technologies or tightly closing technologies may be used. The shield units may be driven manually, or automatically controlled by the control unit 10. As in the present example, an existing shielding technology, such as a shutter, can be used for shielding, which can be easily implemented by a relatively simple configuration.

When the introduction opening 23 or the introduction opening 25 is opened, the ions are introduced into the mass spectrometer 11 for the following reason. The mass spectrometer 11 is evacuated by a rotary pump, a turbo molecule pump or the like. In particular, the degree of vacuum in the analysis unit is 10-5 to 10-6 Torr. Accordingly, there is always a flow of gas from the ion source, which is under atmospheric pressure, via the introduction opening 23 and the flow passageway 21 and into the mass spectrometer 11. In other words, there is the flow from the open introduction opening into the mass spectrometer 11 at all times. Along this flow, not only charged particles such as ions, but also neutral molecules and gases enter the mass spectrometer 11 via the introduction opening 23 or the introduction opening 25.

In the present example, by switching the two analysis modes, two analysis methods can be implemented, one based on the MS mode in which the FAIMS is not passed, and the other on the ion separation mode in which the FAIMS is used. There is no need to manually attach or detach the FAIMS. Once under automatic control, mode switch can be performed within several seconds at high speed. In the MS mode, ions do not pass through the FAIMS. This eliminates the conventional problem of a decrease in the amount of ion due to FAIMS passage, whereby mass spectrometry can be performed when the amount of ion is still high. On the other hand, in the ion separation mode, ion separation is performed by the FAIMS, whereby an analysis can be performed with a high S/N. By switching the two analysis modes, highly efficient data acquisition suitable for the sample can be implemented.

Figure 4:
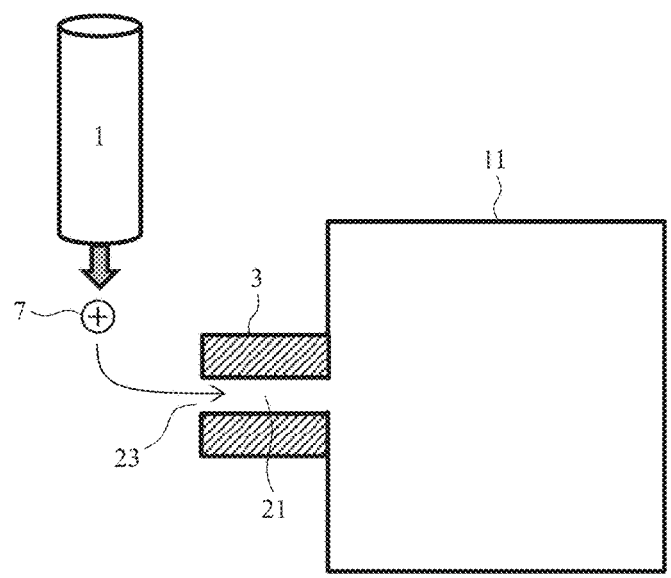
FIG. 4 is a partial cross sectional schematic diagram of the mass spectrometer device as viewed laterally.

FIG. 4 is a partial cross sectional schematic diagram of the mass spectrometer device of the present example, as viewed laterally. The ion source 1, in the case of electrospray ionization (ESI), for example, is configured to deliver a sample solution from top to bottom in the figure, with nebulizer gas and heating gas for atomizing the sample solution flowing from top to bottom. An ion 7 atomized and generated under the ion source 1 is bent by 90 degrees toward the introduction opening 23, for example, and introduced into the mass spectrometer 11 via the flow passageway 21. While not illustrated, the ion is also bent by 90 degrees when being introduced into the introduction opening 25.

As illustrated in FIG. 3A and FIG. 3B, the ion source 1 is enabled to introduce ions into whichever introduction opening among a plurality of introduction openings. Preferably, a plurality of introduction openings may be disposed at equivalent distances from the ion source 1. The equivalent distance means a distance such that the amount of ion introduced from the ion source 1 to each introduction opening can be considered to be equivalent. For example, as illustrated, a plurality of introduction openings may preferably be disposed on a concentric circle 60 about the ion source 1. At the equivalent distances from the ion source 1, the same amount of ion can be introduced from the ion source to any and each of the introduction openings. No matter in which direction on the concentric circle 60 the introduction opening may be located, ion introduction can be performed, as will be readily appreciated from the arrangement in FIG. 4.

The ionization method implemented in the ion source 1 may be an ionization method normally used in a mass spectrometer. Examples include electrospray ionization (ESI); atmospheric pressure chemical ionization (APCI); matrix-assisted laser desorption/ionization (MALDI); desorption electrospray ionization (DESI); and atmospheric pressure photoionization (APPI).

Ion mobility separation devices including FAIMS and DMS are operable under atmospheric pressure or in vacuum.

The mass spectrometer 11 may be a known mass spectrometer. Examples include an ion trap mass spectrometer, such as a three-dimensional ion trap and a linear ion trap; a quadrupole filter mass spectrometer (Q filter); a triple-quadrupole mass spectrometer; a time-of-flight mass spectrometer (TOF/MS); a Fourier transform ion cyclotron resonance mass spectrometer (FTICR); an orbitrap mass spectrometer; and a magnetic sector mass spectrometer. Known mass spectrometers other than the mass spectrometers mentioned above may also be employed.

Figure 5:
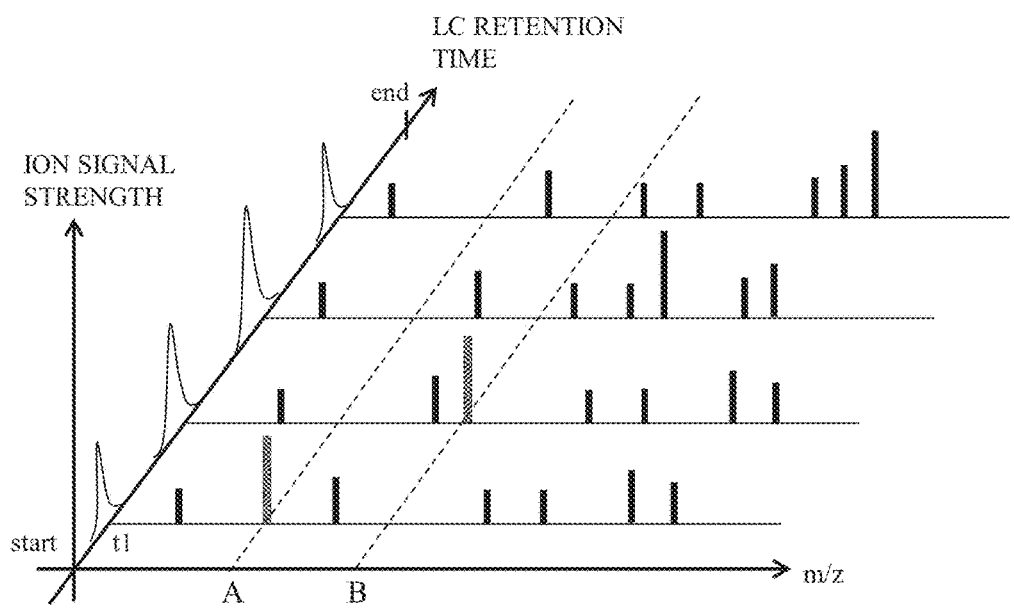
FIG. 5 is a schematic diagram illustrating an example of mass spectrometry data obtained by an LC/MS analysis.

An analysis method implemented by the mass spectrometer device of the present example will be described, with reference to an LC/MS analysis using LC, which is often used in a mass spectrometer. FIG. 5 is a schematic diagram illustrating an example of mass spectrometry data obtained by LC/MS analysis. In LC/MS, a mass spectrum is acquired at each LC retention time. As illustrated in FIG. 5, three-dimensional data consisting of the three axes of LC retention time, m/z, and ion strength are acquired. In FIG. 5, only four mass spectra are shown; in fact, however, a mass spectrum is acquired at all times, including the times at which no ions are detected.

Two analysis methods using the present invention will be described. One is the case in which an analysis ion as a FAIMS target is determined in advance; the other is the case in which the analysis ion is not determined.

[When Target Analysis Ion is Determined]

When the sample ions to be analyzed by the FAIMS are determined, the m/z's of the ions are prepared in advance in List a of analysis ions, as illustrated in FIG. 5. The list may be created by the user in advance. Alternatively, if a list of the m/z's of the ions to be analyzed by the FAIMS is registered in a database, that list may be used. The list and the database are in the control unit 10 and managed by the control unit 10. An example of the list is the List a, in which the m/z's of the sample ions to be analyzed are written. An analysis procedure normally comprises searching for a target ion by acquiring the mass spectrum of the ion in the MS mode, and, if a peak of an ion with the m/z on List a is detected, the mode is switched to the ion separation mode for analysis. For example, at time t1, ion A with m/z=181.1 in the list was detected, so that ion A is analyzed in the ion separation mode.

An analysis method in the ion separation mode will be described. In the ion separation mode, only the target ion is passed mainly through the FAIMS and subjected to mass spectrometry in the mass spectrometer. Because FAIMS have different voltage conditions for analysis depending on the ion species, it is preferable to investigate the analysis conditions in advance. The FAIMS analysis conditions may be registered in a database, i.e., described or prepared in advance in an analysis ion list, as in List b. The list eliminates the need to search for FAIMS analysis conditions, and a target ion analysis can be executed immediately. If the FAIMS analysis conditions for an analysis ion are unclear, it is necessary to spend time and conduct a search. Specifically, it is necessary to perform a scan and determine the FAIMS separating voltage and compensating voltage while monitoring the target ion, so that the amount of the target ion can be increased. In other words, conditions with high S/N may be selected. As to the analysis ion list, by adding the LC retention time to List a, such as in List c, it becomes possible to only analyze the target ion more accurately. Accordingly, the analysis ion lists may be lists that include m/z, LC retention time, and FAIMS separating voltage and compensating voltage. In the mass spectrometry, MS/MS analysis is used with ionic dissociation technology. This method enables an increase in S/N and a more accurate analysis. Ionic dissociation is a method by which ionic dissociation is caused by collision-induced dissociation (CID) and the like, and the generated fragment ions are analyzed. For example, in a triple-quadrupole mass spectrometer, this method is referred to as multiple reaction monitoring (MRM).

[When Target Analysis Ion is Not Determined]

When the analysis ion is not determined in advance, a certain reference is provided during analysis in the MS mode, and, if the reference is satisfied, analysis is performed in the ion separation mode.

1) When a peak with the amount of ion exceeding threshold value has been detected If a peak with the amount of ion not less than a predetermined threshold value has been detected, analysis is performed in the ion separation mode. The threshold value may be designated by the user in advance. If there is a plurality of peaks exceeding the threshold value, analysis is performed with priority given to ions with greater amounts of ion. In addition, by having noise ions and the like noted in the lists, it becomes possible to eliminate noise ions from the analysis object even if the amount of the noise ion is not less than the threshold value.

2) When peak with S/N or S/B not more than threshold value is detected

When a peak with a mass spectrum S/N or S/B smaller than or equal to a pre-set threshold value is detected, analysis is performed in the ion separation mode. The purpose of the present analysis is to achieve an increase in S/N by decreasing noise by performing analysis using the FAIMS.

In this way, by analyzing the target analysis ion in the ion separation mode using the FAIMS, data with high S/N can be acquired. Meanwhile, during a search for an analysis ion, the MS mode may be used to perform the search with high sensitivity. Thus, according to the present example, the MS mode and the ion separation mode can be switched at high speed, and ion analysis can be performed with high efficiency, high throughput, and high sensitivity using the two analysis modes.

Second Example

A second example will be described. In the present example, a gas flow is used as the blocking mechanism to selectively block the passage of the ions from the ion source through the first flow passageway or the second flow passageway for analysis mode switching.

Figure 6A:
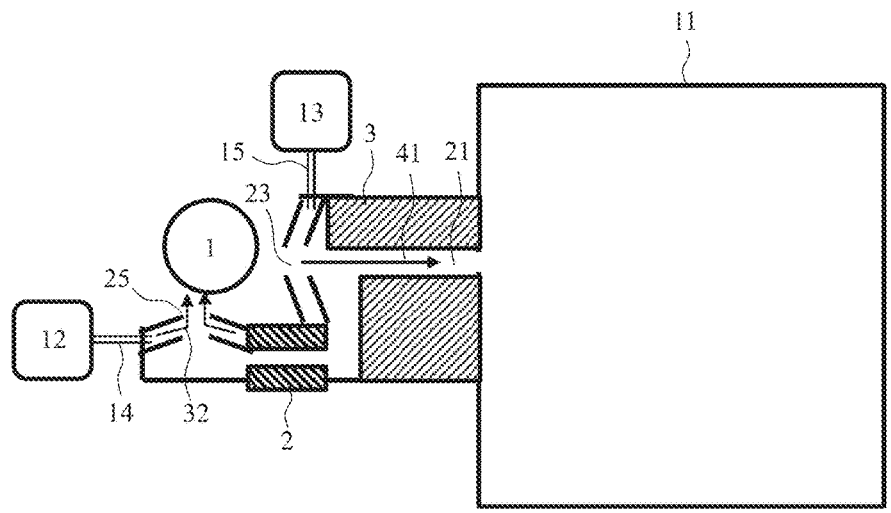
FIG. 6A is a schematic diagram illustrating a configuration example of the mass spectrometer device in MS mode.
Figure 6B:
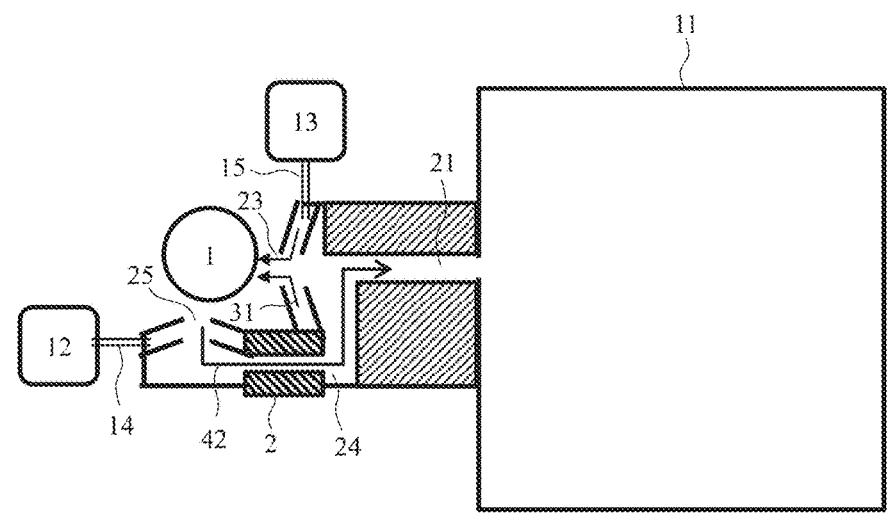
FIG. 6B is a schematic diagram illustrating a configuration example of the mass spectrometer device in ion separation mode.

FIG. 6A and FIG. 6B are partial cross sectional schematic diagrams of the mass spectrometer device of the present example. FIG. 6A illustrates the MS mode, and FIG. 6B illustrates the ion separation mode. The present example differs from the first example in that the blocking mechanism for blocking the passage of ions through the flow passageways employs gas. By causing gas to flow from the mass spectrometer side toward the ion source side, the introduction of ions or neutral molecules into the mass spectrometer can be blocked or prevented.

With reference to FIG. 6A, an example of the MS mode will be described. The gas for blocking the introduction of ions is introduced via a piping 14 using a gas control unit 12. By this introduction of gas, a gas flow 32 is generated at the position of the introduction opening 25 from the mass spectrometer 11 side toward the ion source 1 side. In this way, ions or neutral gas from the ion source 1 can be shielded from entering via the introduction opening 25 toward the FAIMS 2. As a result, the sample ions generated in the ion source 1 can only be introduced via the introduction opening 23, enter the mass spectrometer 11 along the ion trajectory 41 through the flow passageway 21, and are then analyzed. The introduction opening 23 and the introduction opening 25 are circular in shape with a hole diameter on the order of several millimeters to 10 mm. The gas flow rate from the gas control unit 12 necessary for blocking the ions and gas may be on the order of 0.1 L/min to 10 L/min.

It is also possible to use a similar method to block the entry of ions via the introduction opening 23, as illustrated in FIG. 6B. By introducing gas via the piping 15 using the gas control unit 13, a gas flow 31 from the introduction opening 23 toward the ion source 1 can be generated. Due to the introduction of gas, the sample ions are introduced via the introduction opening 25 into the mass spectrometer 11 along the ion trajectory 42 through the flow passageway 24.

The control unit 10, the display unit 18, the input unit 19, and the FAIMS power supply 6 illustrated in FIG. 3A and FIG. 3B, which are not illustrated in FIG. 6A and FIG. 6B for sake of simplification, are used in the same way as in the first example.

In the method according to the present example, a gas flow from the introduction opening toward the ion source is created, whereby the introduction of ions can be blocked and analysis mode switching can be performed. The gas flow can be controlled within one to several seconds. Accordingly, compared with the method using the shield units, the advantage of being able to perform the analysis mode switching at high speed can be obtained, and high throughput analysis can be performed.

Third Example

A third example will be described. In the present example, an electric field is used as the blocking mechanism for selectively blocking the passage of ions from the ion source through the first flow passageway or the second flow passageway for analysis mode switching.

Figure 7A:
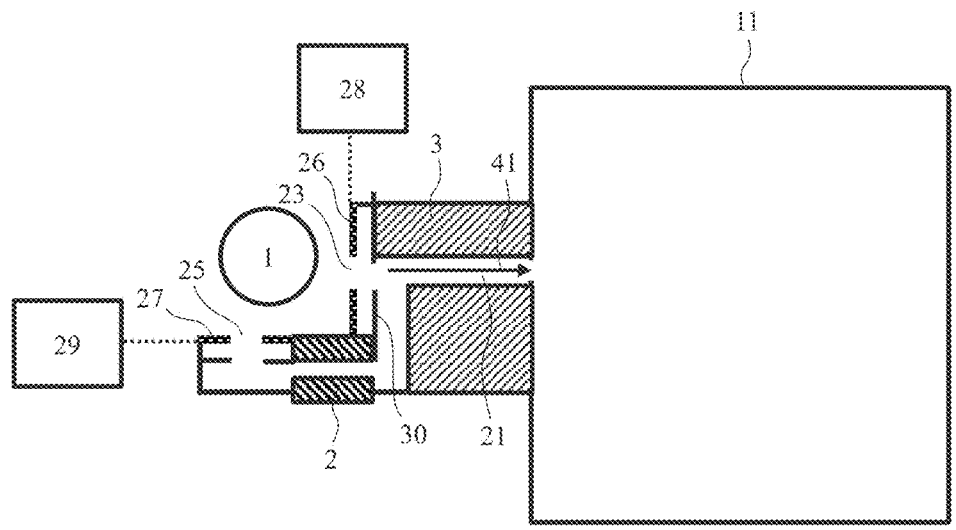
FIG. 7A is a schematic diagram illustrating a configuration example of the mass spectrometer device in MS mode.
Figure 7B:
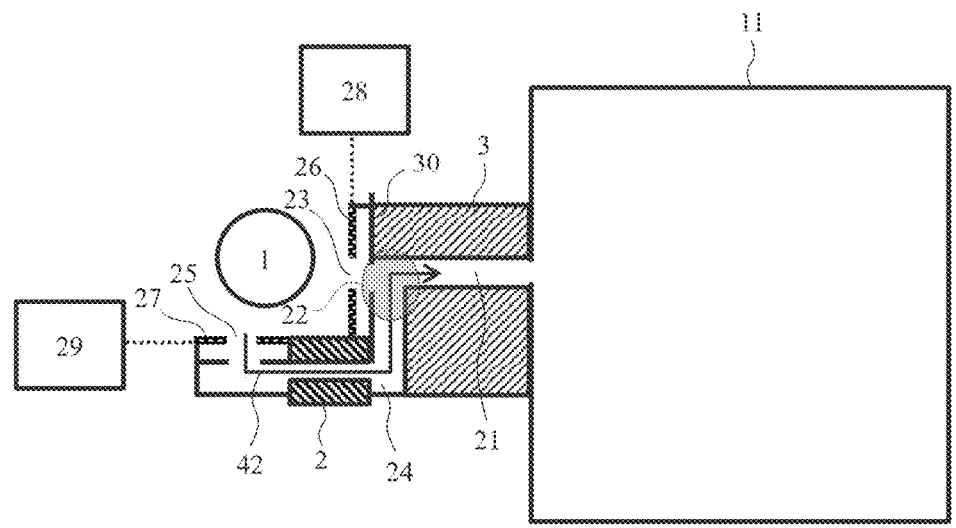
FIG. 7B is a schematic diagram illustrating a configuration example of the mass spectrometer device in ion separation mode.

FIG. 7A and FIG. 7B are partial cross sectional schematic diagrams of the mass spectrometer device of the present example. FIG. 7A illustrates the MS mode, and FIG. 7B illustrates the ion separation mode. The present example differs from the previous examples in that the analysis mode switching is performed by applying voltages to an electrode 26 and an electrode 27 disposed at the flow passageway introduction openings, to thereby block the flow of ions. Because the polarity of the power supply voltage differs depending on whether the sample ion is a positive ion or a negative ion, the present example will be described with reference to an example of positive ion analysis. In the case of a negative ion, a similar method may be implemented by switching the polarity of the power supply voltage. To the electrode 26, a power supply 28 is connected. To the electrode 27, a power supply 29 is connected. Accordingly, direct-current voltages can be applied to the respective electrodes.

Reference is made to the example of the MS mode illustrated in FIG. 7A. In order to block the entry of ions into the introduction opening 25 of the flow passageway communicating with the FAIMS 2, a voltage difference of the electrode 27 with respect to the atomization pipe of the ion source 1 is important. The reason is that atomization by electrospray is caused by a potential difference between the atomization pipe and the electrode 27 (or the electrode 26). While depending on the distance between the two electrodes, i.e., the atomization pipe and the electrode 27 (or the electrode 26), when the distance is on the order of 1 to 30 mm, for example, electrostatic atomization can be caused and ionization can be performed by applying a potential difference on the order of 1000 V to 6000 V between the electrodes. Typically, by applying +5000 V to the atomization pipe of the ion source 1 and +1000 V to the electrode 26, a potential difference of 4000 V is obtained for electrospray ionization. This indicates that electrostatic atomization does not occur and the ions can be blocked on the introduction opening 27 side when the voltage difference between the atomization pipe and the electrode 27 is not greater than 1000 V. In other words, +5000 V may be applied to the atomization pipe, +1000 V may be applied to the electrode 26, and a voltage of not lower than 4000 V, such as +5000 V, may be applied to the electrode 27, for example. In this case, the potential difference between the atomization pipe and the electrode 27 will be zero, whereby the introduction of ions via the introduction opening 25 on the electrode 27 side can be blocked.

In the case of the ion separation mode illustrated in FIG. 7B, +5000 V may be applied to the atomization pipe, +5000 V may be applied to the electrode 26, and +1000 V may be applied to the electrode 27, for example. In this case, the potential difference between the atomization pipe and the electrode 26 will be zero, whereby the introduction of ions via the introduction opening 23 on the electrode 26 side can be blocked.

In the present example, another electrode 30 may preferably be placed in a stage following the electrode 26. In the case of the ion separation mode illustrated in FIG. 7B, the ions entering via the introduction opening 25 travel along the ion trajectory 42 and passes near the electrode 26. Because the electrode 26 is at 5000 V and the introduction opening electrode 3 is typically at approximately 100 V, the ion trajectory may be bent and an ion loss may result as the ions passes through a region 22 near the electrode 26. Accordingly, by installing the electrode 30 in the stage following the electrode 26, and applying a voltage of the same order as that of the introduction opening electrode 3 (for example, 100 V) thereto, the ions are enabled to travel along the ion trajectory 42 without a loss. The electrode 30 may have the same potential as the introduction opening electrode 3. The electrode 30 may be integrated with the introduction opening electrode 3. A structure may be adopted such that the electric field produced when a high voltage is applied to the electrode 26 does not affect the region 22 through which the ions pass. The electrodes 26, 27, and 30 are made of conductive material, such as a metal, and structured with circular openings at the center through which the ions can pass through.

In another example of ion blocking method using an electric field, another electrode may be installed between the electrode 26 and the electrode 30, and a voltage higher than that at the electrode 26 may be applied so as to block ions via the introduction opening 23. The introduction of ions via the introduction opening 25 may similarly be blocked by additionally installing a separate electrode in a stage following the electrode 27. In this method, the separate electrode is disposed in the flow passageways 21, 24 through which ions pass, and a voltage is applied to the electrode so as to form a potential barrier higher than the potential of the ions, thereby blocking the passage of the ions.

In the method according to the present example, the introduction of ions can be blocked by the electric fields generated by applying voltages to the electrodes, whereby analysis mode switching can be performed. The voltages can be controlled at high speed within one second. Accordingly, compared with the previously described methods, the advantage of being able to perform analysis mode switching at high speed can be obtained, and high throughput analysis can be performed.

Fourth Example

A fourth example will be described. In the present example, a gas flow by an exhaust mechanism is used as the blocking mechanism for selectively blocking the passage of ions from the ion source through the first flow passageway or the second flow passageway for analysis mode switching.

Figure 8A:
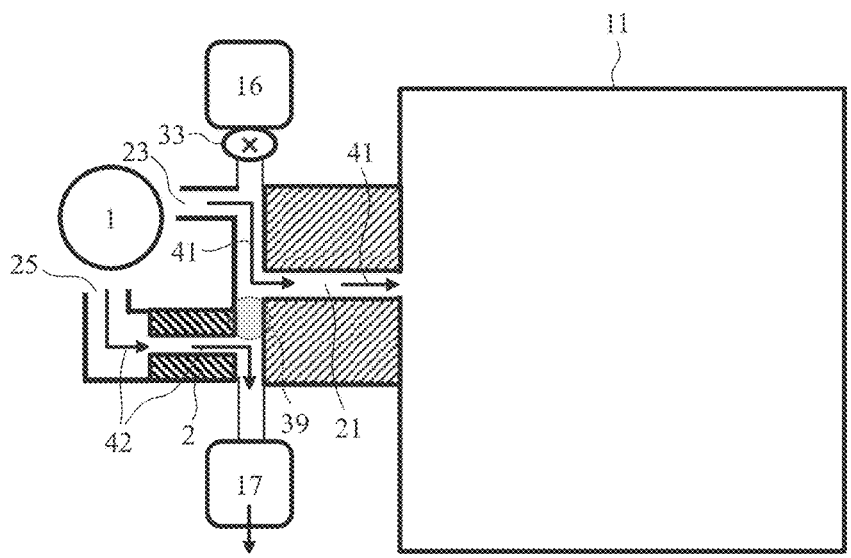
FIG. 8A is a schematic diagram illustrating a configuration example of the mass spectrometer device in MS mode.
Figure 8B:
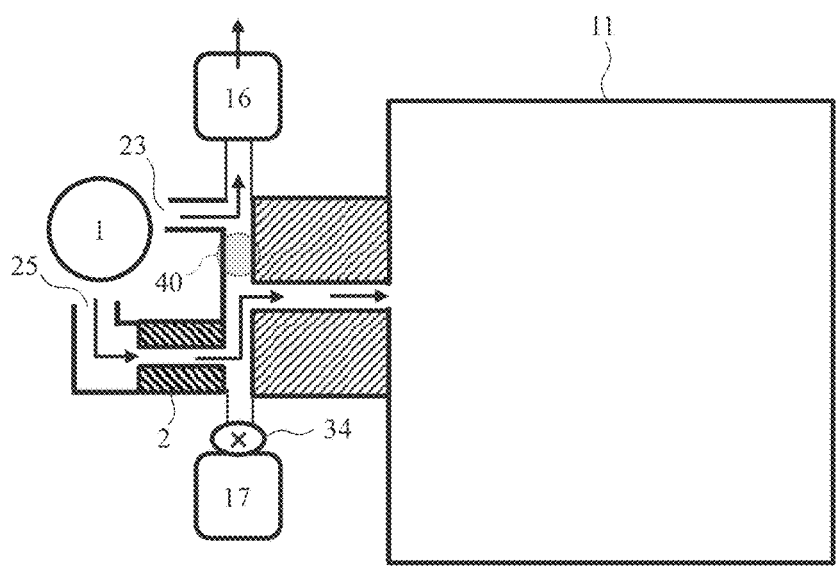
FIG. 8B is a schematic diagram illustrating a configuration example of the mass spectrometer device in ion separation mode.

FIG. 8A and FIG. 8B are partial cross sectional schematic diagrams of the mass spectrometer device of the present example. FIG. 8A illustrates the MS mode, and FIG. 8B illustrates the ion separation mode. As the blocking mechanism, an exhaust unit 16 is connected to the flow passageway following the introduction opening 23. In the illustrated example, the exhaust unit 16 is connected to the downstream side of the introduction opening 23. An exhaust unit 17 is connected to the flow passageway following the introduction opening 25. In the illustrated example, the exhaust unit 17 is connected to the downstream side of the FAIMS. The exhaust units 16, 17 may include fans, exhaust pumps and the like that are capable of generating a gas flow. Preferably, in order to enable a fine and accurate control of flow velocity, a flowmeter or a gas control unit may be provided.

At the time of the MS mode illustrated in FIG. 8A, the exhaust unit 17 is operated, whereby the ions that have passed through the FAIMS are exhausted (suctioned) by the exhaust unit 17 and prevented from reaching the mass spectrometer 11. In this case, the other exhaust unit 16 is either in a state in which the pump is stopped or a state in which the pump is operating but an open/close valve 33 is closed. Accordingly, a gas flow toward the exhaust unit 16 is not generated. The exhaust rate (or exhaust amount) of the exhaust unit 17 is adjusted to be equal to the inflow rate (or inflow amount) via the introduction opening 25. This means that the flow velocity in a region 39 of the flow passageway on the FAIMS side, as viewed from the converging point at which the flow passageway from the introduction opening 23 and the flow passageway from the introduction opening 25 converge, becomes zero (calm). This is a state in which there is no movement of gas or ions above and below the region 39. As a result, the ions entering via the introduction opening 23 are introduced into the mass spectrometer 11 along the ion trajectory 41. Meanwhile, the ions entering via the introduction opening 25 are exhausted into the exhaust unit 17 and eliminated.

During the ion separation mode illustrated in FIG. 8B, the exhaust unit 16 is operated, and the ions introduced via the introduction opening 23 are exhausted by the exhaust unit 16 and prevented from reaching the mass spectrometer 11. In this case, the other exhaust unit 17 is either in a state in which the pump is stopped or a stage in which the pump is operating but the open/close valve is closed. Accordingly, a gas flow toward the exhaust unit 17 is not generated. The exhaust rate of the exhaust unit 16 is adjusted so as to be equal to the inflow rate via the introduction opening 23. This means that the flow velocity in a region 40 of the flow passageway on the introduction opening 23 side, as viewed from the converging point at which the flow passageway from the introduction opening 23 and the flow passageway from the introduction opening 25 converge into one, becomes zero (calm). This is a state in which there is no movement of gas or ions above and below the region 40. As a result, the ions entering via the introduction opening 25 pass through the FAIMS 2 and are introduced into the mass spectrometer 11. Meanwhile, the ions entering via the introduction opening 23 are exhausted into the exhaust unit 16 and eliminated.

Figure 9:
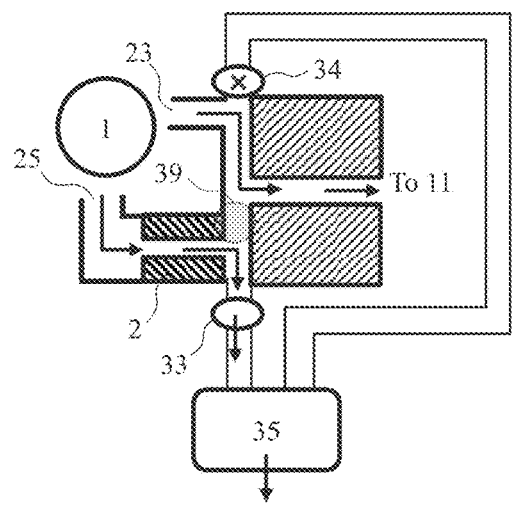
FIG. 9 is a schematic diagram illustrating a configuration example of the mass spectrometer device in MS mode.

FIG. 9 is a schematic diagram illustrating an example of the MS mode according to another aspect of the present example. As illustrated, of the two exhaust units constituting the blocking mechanism, only one exhaust unit 35 may be operated. The piping has the open/close valves (or valves) 33, 34 attached thereto, and by separately opening or closing the valves, the gas flow can be controlled to be switched. In order to obtain the same effective exhaust rates, the exhaust flow passageway through the open/close valve 33 and the exhaust flow passageway through the open/close valve 34 may preferably have the same lengths. Alternatively, the exhaust rates may be adjusted by means of the opening ratios of the open/close valves. As illustrated in FIG. 8A, it is important to adjust the exhaust rate of the exhaust unit 35 so as to make the flow velocity in the region 39 zero.

In the present example, by the gas flow, not only ions but also a gas flow of neutral molecules and the like can be blocked, whereby highly sensitive measurement can be performed.

Fifth Example

A fifth example will be described. In the present example, in a configuration in which a plurality of FAIMSs is mounted, a blocking unit is used as the blocking mechanism for selectively blocking the passage of ions from the ion source through the first flow passageway or the second flow passageway for analysis mode switching.

Figure 10A:
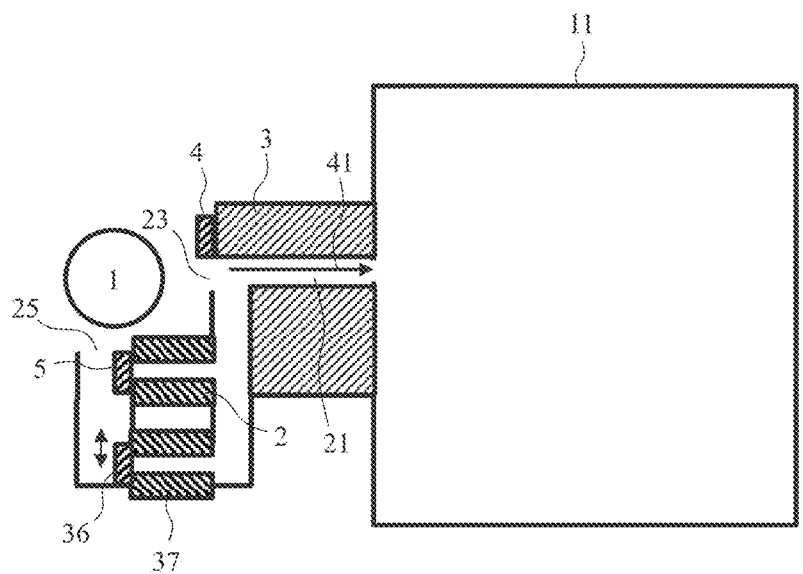
FIG. 10A is a schematic diagram illustrating a configuration example of the mass spectrometer device in MS mode.
Figure 10B:
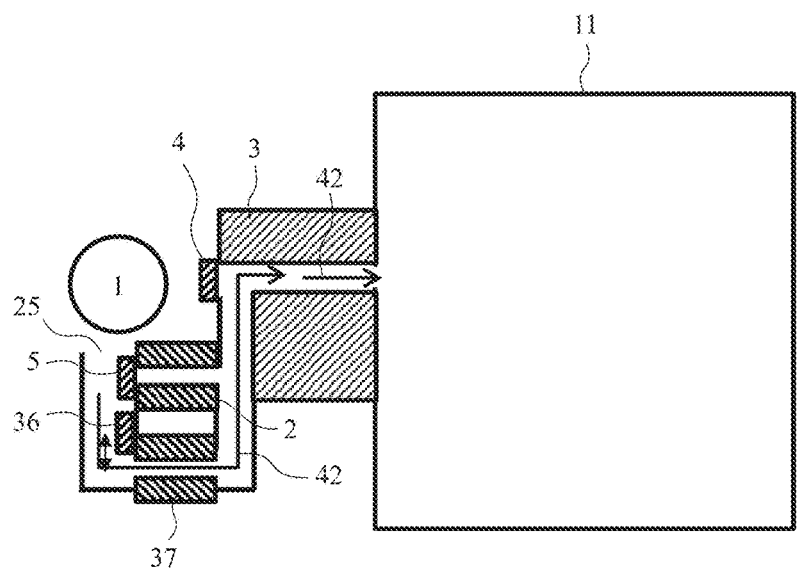
FIG. 10B is a schematic diagram illustrating a configuration example of the mass spectrometer device in ion separation mode.

FIG. 10A and FIG. 10B are partial cross sectional schematic diagrams of the mass spectrometer device of the present example. FIG. 10A illustrates the MS mode, and FIG. 10B illustrates the ion separation mode. The method switches a total of three modes of the MS mode and two ion separation modes.

At the entrances to the FAIMS 2 and a FAIMS 37, a blocking unit 5 and a blocking unit 36 are respectively installed as the blocking mechanism. In the flow passageway that does not pass through the FAIMSs, the blocking unit 4 is installed. While not illustrated, the blocking units are connected to respective drive units, as in the foregoing examples, and can be operated by the control unit 10.

FIG. 10A illustrates the MS mode in which the FAIMSs are not passed through, where the blocking unit 4 is opened, and the ions travel through the flow passageway 21 and are introduced into the mass spectrometer 11 along the ion trajectory 41. In this case, because the blocking unit 5 and the blocking unit 36 are closed, the ions are not introduced into the FAIMSs 2, 37. FIG. 10B illustrates the ion separation mode in which the ions are passed only through the FAIMS 37. While the blocking units 4, 5 are closed, the blocking unit 36 is open, allowing the passage of the ions only to the FAIMS 37. The ions that have passed through the introduction opening 25 travel through the FAIMS 37, are introduced into the mass spectrometer 11 along the ion trajectory 42, and then analyzed therein. Accordingly, the blocking mechanism selectively permits the passage of the ions from the ion source through one of the first FAIMS 2, the second FAIMS 37, or the introduction opening 23, and blocks the others.

The two FAIMSs are mounted for two major reasons. One is for the cleaning and maintenance of the FAIMSs, and the other is to provide a FAIMS with a different separation performance. With regard to the first reason, i.e., cleaning and maintenance, two FAIMSs with the same structure are mounted, of which one is stocked for cleaning and maintenance or as a backup, and the other FAIMS is used for analysis. In this method, an analysis need not be stopped in the event of a problem in the FAIMS during analysis or when cleaning is required, and the other FAIMS can be used immediately for analysis. During the analysis, the FAIMS can be maintained or cleaned. The method eliminates the need to stop analysis for FAIMS maintenance, whereby the throughput of analysis increases.

The second reason is that it becomes possible to install a FAIMS with a different separation performance. For example, by installing a FAIMS having a different interval of the two plate electrodes constituting the FAIMS, an analysis can be performed with a different separation performance. The separation performance is mainly determined by the interval or length of the plate electrodes constituting the FAIMS. Accordingly, by installing two FAIMSs with a 0.5 mm interval and a 1 mm interval, different separation performances can be obtained or different amounts of ion data can be acquired. It is also effective to install two FAIMSs with different FAIMS lengths on the order of between 10 mm to 100 mm. In addition, one may be configured to cause a flow of reaction sample in the FAIMS. For example, by introducing a gas mixture of trace amounts of isopropanol, methanol, acetone and the like into the FAIMS, the separating performance can be varied, whereby different ion separation can be performed. In this way, by installing a plurality of FAIMSs having different separating performances, various substances can be analyzed effectively.

Figure 11A:
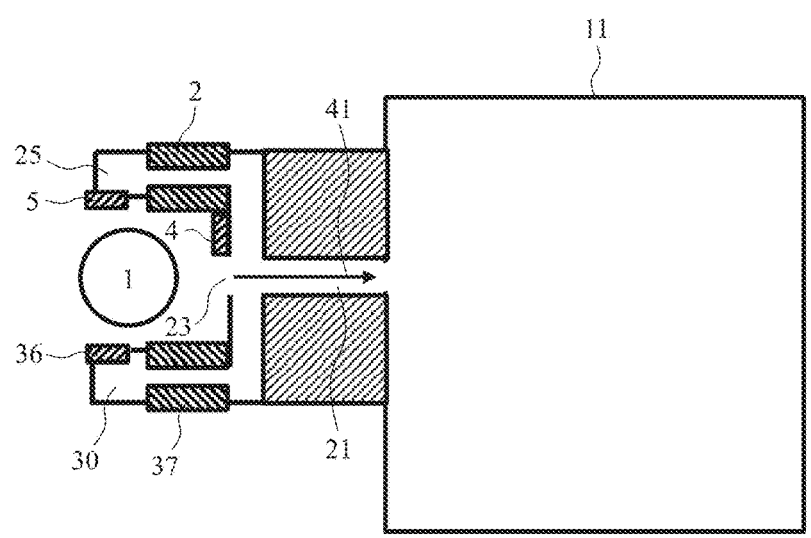
FIG. 11A is a schematic diagram illustrating a configuration example of the mass spectrometer device in MS mode.
Figure 11B:
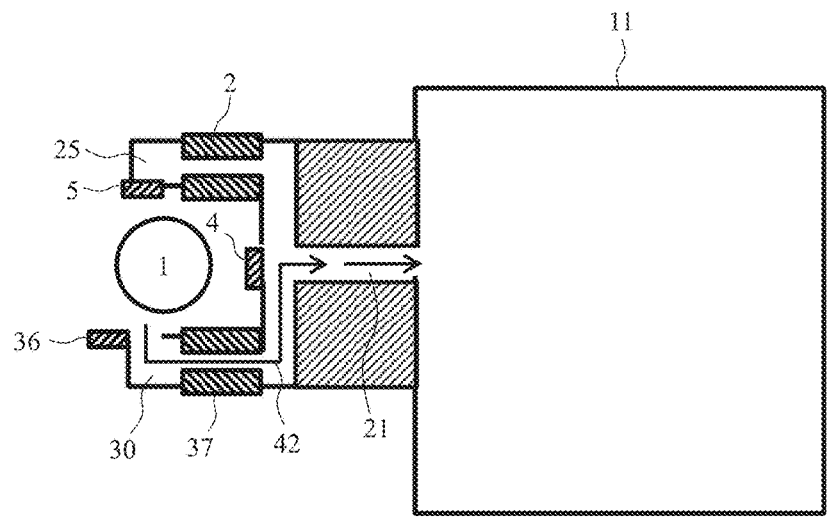
FIG. 11B is a schematic diagram illustrating a configuration example of the mass spectrometer device in ion separation mode.

FIG. 11A and FIG. 11B illustrate another configuration example of the present example. In this example, the FAIMSs are disposed symmetrically on either side. FIG. 11A illustrates the MS mode, and FIG. 11B illustrates the ion separation mode. The contents of implementation are the same as those of the examples of FIG. 10A and FIG. 10B. In this configuration, as viewed in the drawing figures, the introduction openings 23, 25, and 30 are respectively disposed in three directions with respect to the ion source.

Herein, the configurations using two FAIMSs have been described. While the three flow passageways for the MS mode and the two FAIMS ion separation modes have been described as being disposed on the same plane, this is for illustrative purpose, and the flow passageways may not necessarily be all disposed on the same plane.

As described in the foregoing examples, the analysis mode switching method of the present examples may be implemented by methods using gas, an electric field, or an exhaust unit. The number of the FAIMSs is not limited to two, and three or more FAIMSs may be used for a similar implementation.

Sixth Example

Figure 12:
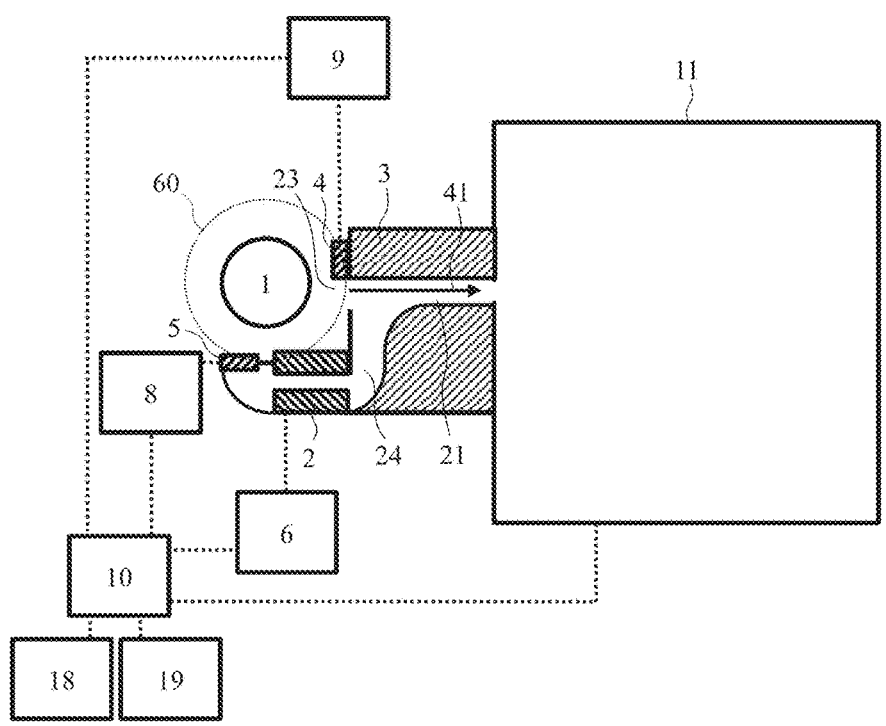
FIG. 12 is a schematic diagram illustrating a configuration example of the mass spectrometer device in MS mode.

A sixth example will be described. FIG. 12 is a partial cross sectional schematic diagram illustrating the MS mode of the mass spectrometer device of the present example. The flow passageway described in the first example with reference to FIG. 3A and FIG. 3B is deformed so that the structure allows ions to smoothly flow from the flow passageway 24 to the flow passageway 21. The flow passageway structure can be expected to enable efficient introduction of ions into the mass spectrometer 11. Other details of the implementation method are similar to those of the first example.

Seventh Example

A seventh example will be described. In the foregoing examples, there is one flow passageway connecting to the mass spectrometer 11. In the present example, two flow passageways are provided.

Figure 13A:
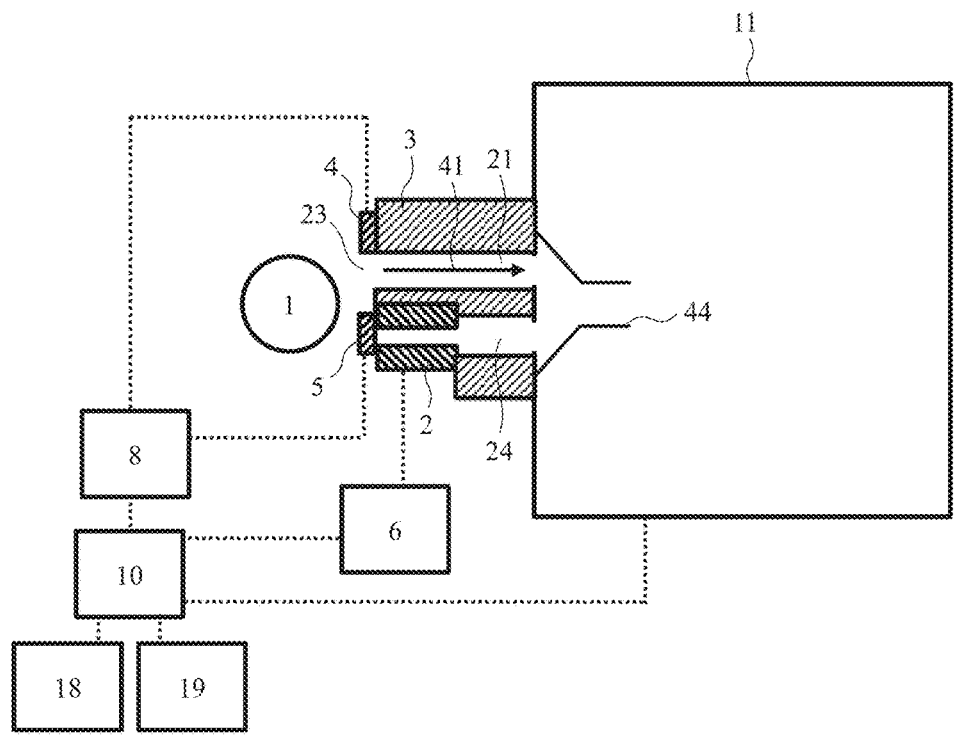
FIG. 13A is a schematic diagram illustrating a configuration example of the mass spectrometer device in MS mode.
Figure 13B:
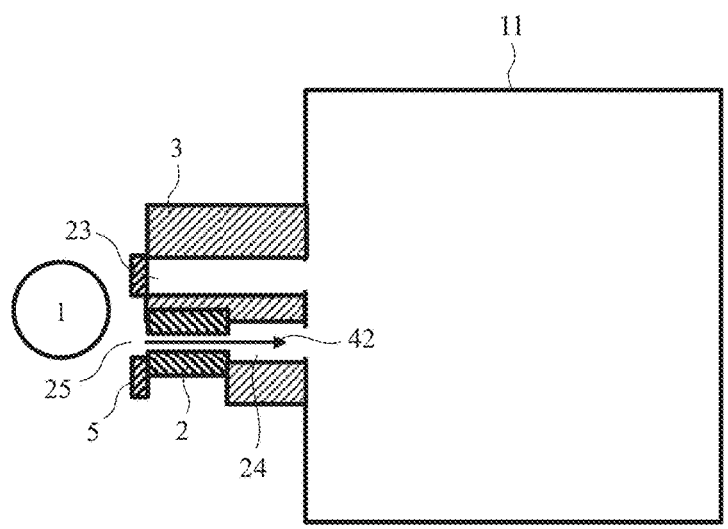
FIG. 13B is a schematic diagram illustrating a configuration example of the mass spectrometer device in ion separation mode.

FIG. 13A and FIG. 13B are partial cross sectional schematic diagrams of the mass spectrometer device of the present example. FIG. 13A illustrates the MS mode, and FIG. 13B illustrates the ion separation mode. In FIG. 13A, the shield unit 4 of the blocking mechanism for opening and closing the introduction opening 23 is opened. Accordingly, the ions entering via the introduction opening 23 travel through the flow passageway 21 and are introduced into the mass spectrometer 11. On the other hand, the shield unit 5 for opening and closing the introduction opening 25 is closed. Accordingly, the ions are not introduced into the introduction opening 25. In FIG. 13B, conversely, the introduction opening 23 is closed and the introduction opening 25 is opened. Accordingly, the ions entering via the introduction opening 25 travel through the FAIMS 2 and the flow passageway 24, and are introduced into the mass spectrometer 11. Thus, ion separation can be performed using the FAIMS. In the present example, the flow passageway 21 and the flow passageway 24 are connected in parallel to the mass spectrometer.

The introduction opening electrode 3 has a flow passageway inner diameter on the order of not more than 1 mm. The flow passageways 21, 24 have an interval on the order of several millimeters. Accordingly, the ions in the two flow passageways enter at a distance of approximately 5 mm. Accordingly, it is preferable to attach an ion converging electrode 44 in a stage following the introduction opening electrode 3. In order to enable the converging of the ions, the ion converging electrode 44 may comprise a funnel-shaped electrode to which a direct-current voltage is applied, or an existing, ring-shaped ion guide comprising an arrangement of a plurality of ring electrodes to which an alternating-current voltage is alternately applied. Also, as illustrated in FIG. 14, the ions may also be focused by means of a multipole ion guide 45, such as a quadrupole or octupole ion guide, as known in the art.

Figure 14:
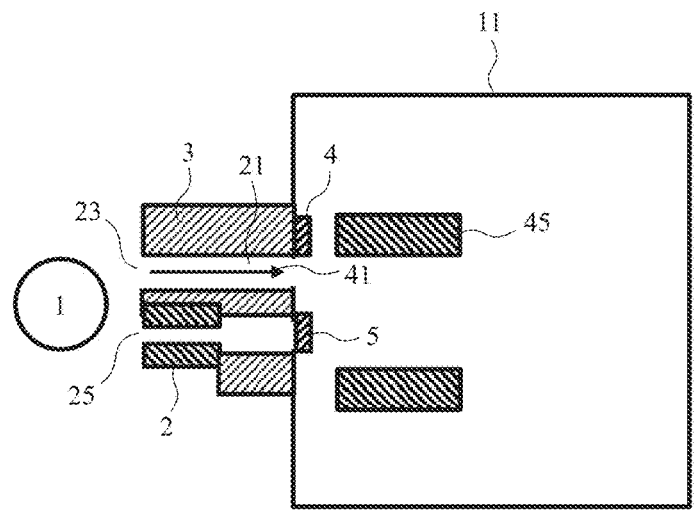
FIG. 14 is a schematic diagram illustrating a configuration example of the mass spectrometer device in MS mode.

FIG. 14 illustrates another configuration example of the present example. In this example, the shield units 4, 5 constituting the blocking mechanism are installed not on the ion source side but on the mass spectrometer 11 side. In this configuration, because the shield units are located on the mass spectrometer 11 side, the flow passageway can be expected to be shielded more tightly. While the diagram only illustrates the MS mode, the ion separation mode may have a configuration similar to that of the preceding examples.

Figure 15:
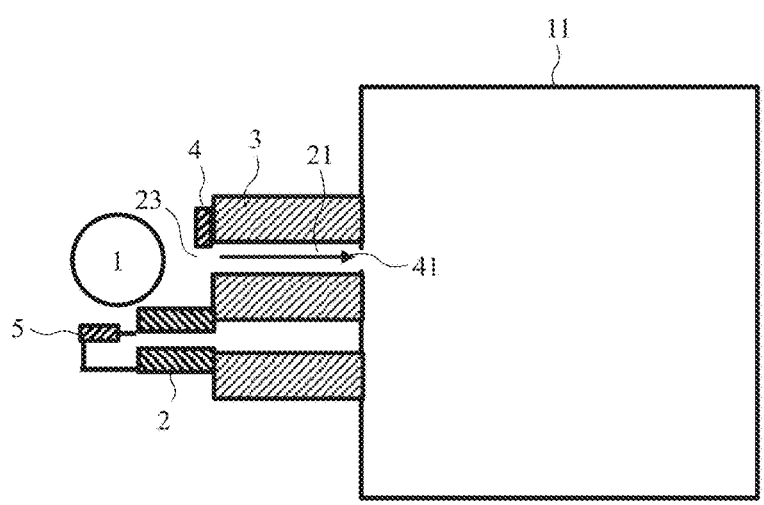
FIG. 15 is a schematic diagram illustrating a configuration example of the mass spectrometer device in MS mode.

FIG. 15 illustrates another configuration example of the present example. With respect to the ion source 1, the introduction opening 23 and the introduction opening 25 are attached at angles differing by 90 degrees. Other configurations are similar to those of the preceding examples. The diagram illustrates the MS mode.

Figure 16:
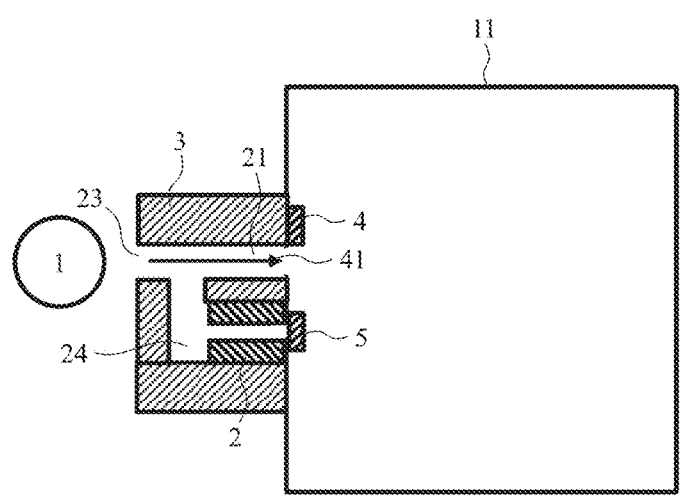
FIG. 16 is a schematic diagram illustrating a configuration example of the mass spectrometer device in MS mode.

FIG. 16 illustrates yet another configuration example of the present example. In this configuration, while there is one introduction opening 23 from the ion source 1, the introduction opening 23 diverges to the flow passageway 21 and the flow passageway 24. That is, the flow passageway 21 and the flow passageway 24 share the introduction opening 23. In the flow passageway 24, the FAIMS 2 is attached. In this configuration, the shield units 4, 5 constituting the blocking mechanism are installed on the mass spectrometer 11 side. The mode switching is implemented by selectively driving the shield units 4, 5.

While the present example has been described with reference to two flow passageways connecting to the mass spectrometer 11, a similar implementation is also possible with three or more flow passageways.

Instead of the shield units 4, 5, the ion shield using gas or the ion shield using an electric field as described above may also be used to implement the mode switching in a similar manner.

The present invention is not limited to the foregoing examples, and may include various modifications. The foregoing examples have been described for the purpose of facilitating an understanding of the present invention, and are not necessarily limited to those having the described configurations in their entirety. Part of the configuration of one example may be replaced with the configuration of another example, or the configuration of the other example may be incorporated into the configuration of the one example. With respect to part of the configuration of each of the examples, addition, deletion, or substitution of other configurations may be possible.

REFERENCE SIGNS LIST

1 Ion source
2 FAIMS
3 Introduction opening electrode
4 Shield unit
5 Shield unit
6 FAIMS power supply
7 Ion
11 Mass spectrometer
12, 13 Gas control unit
16, 17 Exhaust unit
20 Electrode
23 Introduction opening
25 Introduction opening
26, 27 Electrode
30 Electrode
33, 34 Open/close valve
44 Ion converging electrode
45 Multipole ion guide

The invention claimed is:

1. A mass spectrometer device comprising:
an ion source;
an ion mobility separation unit;
a mass spectrometer;
a first flow passageway for causing ions from the ion source to be introduced into the mass spectrometer by passing through the ion mobility separation unit;
a second flow passageway for causing the ions from the ion source to be introduced into the mass spectrometer without passing through the ion mobility separation unit; and
a blocking mechanism for selectively blocking the passage of the ions from the ion source through the first flow passageway or the second flow passageway,
wherein an introduction opening of the first flow passageway and an introduction opening of the second flow passageway are disposed at equivalent distances from the ion source.

2. The mass spectrometer device according to claim 1, wherein the blocking mechanism comprises a first shield unit that shields the first flow passageway, a first drive unit that drives the first shield unit, a second shield unit that shields the second flow passageway, and a second drive unit that drives the second shield unit.

3. The mass spectrometer device according to claim 1, wherein the blocking mechanism comprises a first gas control unit that causes a gas flow from an introduction portion of the first flow passageway toward the ion source, and a second gas control unit that causes a gas flow from an introduction portion of the second flow passageway toward the ion source.

4. The mass spectrometer device according to claim 1, wherein the blocking mechanism comprises a first electrode disposed in an introduction portion of the first flow passageway, a first power supply that applies a voltage to the first electrode, a second electrode disposed in an introduction portion of the second flow passageway, and a second power supply that applies a voltage to the second electrode,
   wherein electrostatic atomization is caused between the electrode side of only one of the first electrode and the second electrode and the ion source.

5. The mass spectrometer device according to claim 1, wherein the blocking mechanism comprises a first electrode disposed in the first flow passageway, a first power supply that applies a voltage to the first electrode, a second electrode disposed in the second flow passageway, and a second power supply that applies a voltage to the second electrode,
   wherein a potential barrier higher than a potential of the ions from the ion source is selectively formed in the first flow passageway or the second flow passageway.

6. The mass spectrometer device according to claim 1, wherein the blocking mechanism comprises a first exhaust unit connected to the first flow passageway, and a second exhaust unit connected to the second flow passageway,
   wherein one the first exhaust unit and the second exhaust unit is selectively operated.

7. The mass spectrometer device according to claim 1, wherein the first flow passageway and the second flow passageway are integrated into one flow passageway connected to the mass spectrometer.

8. The mass spectrometer device according to claim 1, wherein the first flow passageway and the second flow passageway are connected in parallel to the mass spectrometer.

9. The mass spectrometer device according to claim 1, wherein the first flow passageway and the second flow passageway share the introduction openings.

10. The mass spectrometer device according to claim 1, wherein the ion mobility separation unit is a FAIMS.

11. The mass spectrometer device according to claim 1, wherein the ion mobility separation unit comprises a first FAIMS and a second FAIMS,
    wherein the blocking mechanism selectively permits one of the passages of the ions from the ion source through the first FAIMS, through the second FAIMS, or through the second flow passageway, and blocks the others.

12. The mass spectrometer device according o claim 1, wherein, during analysis in the mass spectrometer of the ions that have passed through the second flow passageway, upon detection of a peak of an ion having a mass to charge ratio that has been registered in advance, the blocking mechanism blocks the second flow passageway and allows the ion to pass through the first flow passageway.

13. The mass spectrometer device according to claim 1, wherein, during analysis in the mass spectrometer of the ions that have passed through the second flow passageway, upon detection of a peak with a mass spectrum S/N smaller than or equal to a pre-set threshold value, the blocking mechanism blocks the second flow passageway and allows the ions to pass through the first flow passageway.

* * * * *